(12) United States Patent
Erkens et al.

(10) Patent No.: US 11,298,303 B2
(45) Date of Patent: Apr. 12, 2022

(54) SYSTEM FOR THICKENING A DYE PREPARATION CONTAINING PERCARBONATE

(71) Applicant: Henkel AG & Co. KGaA, Duesseldorf (DE)

(72) Inventors: Udo Erkens, Willich (DE); Torsten Lechner, Langenfeld (DE); Carsten Mathiaszyk, Essen (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 0 days.

(21) Appl. No.: 16/719,734

(22) Filed: Dec. 18, 2019

(65) Prior Publication Data
US 2020/0206099 A1    Jul. 2, 2020

(30) Foreign Application Priority Data

Dec. 28, 2018  (DE) .................... 10 2018 133 677.2
Feb. 28, 2019  (DE) .................... 10 2019 105 165.7

(51) Int. Cl.
| | |
|---|---|
| *A61Q 5/10* | (2006.01) |
| *A61K 8/19* | (2006.01) |
| *A61K 8/73* | (2006.01) |
| *A61K 8/46* | (2006.01) |
| *A61K 8/41* | (2006.01) |
| *A61K 8/34* | (2006.01) |
| *A61K 8/25* | (2006.01) |
| *A61K 8/11* | (2006.01) |
| *A61K 8/81* | (2006.01) |

(52) U.S. Cl.
CPC ............... *A61K 8/19* (2013.01); *A61K 8/11* (2013.01); *A61K 8/25* (2013.01); *A61K 8/347* (2013.01); *A61K 8/411* (2013.01); *A61K 8/415* (2013.01); *A61K 8/463* (2013.01); *A61K 8/731* (2013.01); *A61K 8/737* (2013.01); *A61K 8/8129* (2013.01); *A61Q 5/10* (2013.01); *A61K 2800/48* (2013.01); *A61K 2800/5922* (2013.01); *A61K 2800/87* (2013.01)

(58) Field of Classification Search
CPC . A61Q 5/10; A61K 8/411; A61K 8/22; A61K 8/415; A61K 8/19; A61K 2800/4324; A61K 8/347; A61K 8/731; A61K 2800/48
USPC ........................................................ 8/405
See application file for complete search history.

(56) References Cited

U.S. PATENT DOCUMENTS

| | | | |
|---|---|---|---|
| 10,987,287 B2* | 4/2021 | Erkens ................... | A61K 8/737 |
| 2014/0082854 A1* | 3/2014 | Landa ................ | G01N 33/4833 |
| | | | 8/405 |

FOREIGN PATENT DOCUMENTS

| | | |
|---|---|---|
| EP | 2361604 A1 | 8/2011 |
| EP | 3473238 A1 | 4/2019 |
| EP | 3086859 B1 | 5/2019 |
| WO | 2018114886 A1 | 6/2018 |

* cited by examiner

*Primary Examiner* — Eisa B Elhilo
(74) *Attorney, Agent, or Firm* — Lorenz & Kopf, LLP

(57) ABSTRACT

The present falls within the field of cosmetics and relates to a cosmetic product for oxidatively changing the colour of keratinous fibres, particularly human hair. An exemplary cosmetic product includes (i) at least one cosmetic composition (KM) comprising (a) at least one oxidising compound, and (b) two or more thickening agents, and (ii) at least one cosmetic dye composition (FZ). The oxidising compound is a solid oxidising agent and is selected from the group of a percarbonate salt, a perborate salt and percarbamide salt. Further, the two or more thickening agents comprise an at least partially ionic polysaccharide and a substantially non-ionic polysaccharide. Also described is a method for dyeing hair.

10 Claims, No Drawings

SYSTEM FOR THICKENING A DYE PREPARATION CONTAINING PERCARBONATE

CROSS-REFERENCE TO RELATED APPLICATION

This application claims priority to German Patent Application No. 10 2019 105 165.7, filed Feb. 28, 2019, and which claims priority to German Patent Application No. 10 2018 133 677.2, filed Dec. 28, 2018, which are both incorporated herein by reference in their entirety.

TECHNICAL FIELD

The present disclosure falls within the field of cosmetics and relates to a cosmetic product for oxidative dyeing of keratinous fibres, particularly human hair, which product includes a composition that contains an oxidising agent. The composition that contains an oxidising agent includes a thickening agent. The oxidising compound is a solid compound which includes a percarbonate salt, a perborate salt or a percarbamide salt. The present disclosure further relates to a method for dyeing hair.

BACKGROUND

Changing the colour of keratinous fibres, particularly hair, represents an important area of modern cosmetics. In this way, the appearance of the hair can be adapted to reflect both current fashion trends and the personal preferences of the individual. The person skilled in the art knows various ways to change hair colour.

Hair colour can be changed temporarily through the use of direct dyes. In this context, pre-constituted colouring agents diffuse out of the dye into the hair fibres. Dyeng with direct colouring agents causes only mild damage to the hair, but a drawback of this process is that it does not last long, and the direct colours obtained with direct colouring agents can be washed out rapidly.

For this reason, oxidative dyeing agents are used as a rule if the consumer desires a long lasting colouring result or a shade that is lighter than his/her original hair colour. For permanent, rich colouring with corresponding fastness properties, "oxidation dyes" are used. Such dyes usually contain oxidising dye precursors, called developer components and coupler components, which under the effect of oxidising agents—most often hydrogen peroxide—combine to form the actual colouring agents. Oxidation dyes are noted for their excellent, long-lasting colouring results.

Simple lightening or blonding of hair is often carried out using oxidising agents, without the addition of oxidising dye precursors. For a moderate blonding effect, it is sufficient to use hydrogen peroxide alone as the oxidising agent, a more pronounced blonding effect typically requires the use of a mixture of hydrogen peroxide and peroxydisulfate salts.

Oxidative colouring agents on the commercial market usually have the form of bi-component media in which two different preparations are present, ready for use and supplied in two separate packages, and are not mixed with each other until shortly before their application.

The first preparation is a formulation—typically adjusted with acid for reasons of stability which contains for example liquid hydrogen peroxide in concentrations from about 1.5 to about 12 wt % as the oxidising agent. The oxidising agent formulation is usually in the form of an emulsion or a dispersion, and is typically provided in a plastic bottle with a reclosable outlet opening (developer bottle).

This oxidising agent formulation is mixed with a second preparation before application. This second preparation is a formulation which is adjusted with an alkali and often has the form of a lotion or gel and, if the user wishes to lighten their hair as well as changing its colour, also contains at least one oxidising dye precursor. This second preparation may be provided in a tube or in a plastic or glass container for example.

In the usual application form described in the preceding text, the second preparation containing the alkalising agent and/or the oxidising dye precursor is transferred out of the tube or container and into the developer bottle and then mixed with the hydrogen peroxide preparation which is already in the developer bottle by shaking. In this way, the application mixture is produced in the developer bottle. It is then spread on the hair through a small nozzle or outlet opening on the head of the developer bottle. The nozzle or outlet opening is opened after shaking, and the application mixture can be expressed from the flexible developer bottle by squeezing.

If the application mixture is produced in a dish, both components—the first preparation containing the oxidising agent and the second preparation with the alkalising agent and/or oxidising dye precursors—are transferred completely to a dish or similar receptacle and stirred there with the aid of a brush, for example. The application mixture is then removed from the mixing dish on the brush. With this form of application, it is not necessary to use a bulky, expensive developer bottle.

However, filling such packages with the oxidising agent preparations is associated with problems whose fundamental causes are linked to the reactivity of the oxidising agent. Oxidising agents are strongly reactive, usually fluid or paste-like substances which a broken down into small components, forming oxygen (i.e. gas) as a consequence of the conditions in which they are stored and the presence of any contaminants with decomposing effect.

The developer bottles known from the related art are typically not filled to more than half their capacity, often to only a third of their internal volume with the oxidising agent composition. Developer bottles are typically made from polyethylene. Since polyethylene is permeable to both water vapour and gases, very little or no positive pressure is created in the developer bottle. Moreover, developer bottles usually have strong, thick walls and are fitted with a sturdy screw closure, so that diffusion of the water vapour and gases through the thickness of the walls is reduced, and the limited increase in pressure inside the bottle has no negative effects.

Consequently, the packaging products are usually bulky, which in turn is detrimental in terms of environmental and resource conservation. An advantage might be made possible if a solid were used as the oxidising agent. Then, oxidising dye precursors and oxidising agents might also be provided in one container, since the reaction of the components necessitates mixing with water. Persulfates and percarbonates are known as solid oxidising agents for dye preparations. They are used in the form of salts. However, the use of salts is disadvantageous for adjusting the viscosity of the ready-to-use cosmetic composition. This is because in many cases the thickening agents used are polyelectrolytes such as xanthan gum, which lose their ability to raise viscosity as the salt content increases. If the viscosity of the ready-to-use hair dye composition is too low, its application is less pleasant, so the handling properties of the substance are impaired.

BRIEF SUMMARY

A cosmetic product and method for colouring keratinous fibres are provided. In an exemplary embodiment a cosmetic product for changing the natural colour of keratinous fibres includes (i) at least one cosmetic composition (KM) comprising (a) at least one oxidising compound, and (b) two or more thickening agents, and (ii) at least one cosmetic dye composition (FZ). The oxidising compound is a solid oxidising agent and is selected from the group of a percarbonate salt, a perborate salt and percarbamide salt. Further, the two or more thickening agents comprise an at least partially ionic polysaccharide and a substantially non-ionic polysaccharide.

In another exemplary embodiment, a method for colouring keratinous fibres includes mixing a cosmetic product according to claim 1 with water to form a mixture, applying the mixture to the keratinous fibres immediately thereafter, leaving the mixture on the keratinous fibres for 5 to 60 minutes, and rinsing the keratinous fibres with water and optionally washing the keratinous fibres with a tenside-containing cleaning agent.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The problem addressed by the present application is that of providing a hair dye that comprises a solid oxidising agent, wherein the hair dye is not associated with any disadvantages in respect of handling, particularly in terms of the viscosity of the ready-to-use hair dye. A further problem is that it should be possible to package the hair dye formulations in such manner that they can be stored reliably and economically in terms of space.

The problem addressed by the present disclosure is solved with the object of claim 1. A first object of the present disclosure is therefore a cosmetic product for changing the natural colour of keratinous fibres, particularly human hair, which comprises (i) at least one cosmetic composition (KM) containing: a) at least one oxidising compound and b) two or more thickening agents, and (ii) at least one cosmetic dye composition (FZ), wherein the oxidising compound is a solid oxidising agent and is selected from the group including a percarbonate salt, a perborate salt and percarbamide salt, wherein the two or more thickening agents include an at least partly ionic polysaccharide and a substantially non-ionic polysaccharide.

Keratinous fibres, keratin-containing fibres or keratin fibres are understood to include furs, wool, feathers, and in particular human hair. Although the media as contemplated herein are primarily designed for lightening and colouring keratin fibres, in principle there is no reason why they may not be used in other fields.

The product as contemplated herein is a product for oxidatively changing the colour of keratinous fibres, i.e. a product which is applied to the human head to bring about oxidative dyeing or lightening of the hair. In this context, "lightening" is understood to mean a colouring process in which the colour result is lighter than the original hair colour. In the application as a whole, the term "cosmetic dye composition (FZ)" is used interchangeably with the terms "preparation (FZ)" or "dye composition (FZ)", and the term "cosmetic composition (KM)" is used interchangeably with the term "preparation (KM)".

The product as contemplated herein comprises as the first constituent a cosmetic composition (KM) which contains at least one oxidising compound, specifically a solid oxidising agent, and a thickening agent.

The cosmetic composition (KM) contains as the first essential ingredient a) at least one oxidising compound. Therefore, it is particularly advantageous within the scope of the present disclosure that the cosmetic composition (KM) contain at least solid oxidising agent. When a solid oxidising agent is used, the oxidising compound and die cosmetic dye composition may be kept in one container, since without the addition of water the solids only react in negligible quantities and over a relatively long period of time. Expensive packing features for liquid hydrogen peroxide may be dispensed with.

The solid oxidising agent represents a substitute for the free hydrogen peroxide which is used in the dyes of the related art. Free hydrogen peroxide means a hydrogen peroxide in liquid solution. The solid aggregate state refers to standard conditions, i.e., about 20° C. and about $10^5$ Pa, when the oxidising agent is present in undissolved form, i.e. without a solvent or diluent. Unless otherwise indicated, all data regarding the aggregate state refer to these standard conditions.

In the course of the work leading to this present disclosure, it was found that the product as contemplated herein also lends itself well to advantageous packaging and stable storage. Thus, packaged cosmetic products as contemplated herein exhibited no changes in volume (i.e. no swellings) and no unplanned openings (i.e. the packages did not rupture) even after being stored at elevated temperature for several weeks.

As contemplated herein, the solid oxidising agent is a percarbonate salt, a perborate salt and/or a percarbamate salt. The term percarbamide is used to describe an additive compound including hydrogen peroxide and urea. A percarbonate may preferably be understood to describe a $H_2O_2$ adduct. For example, the particularly preferred sodium percarbonate is substance having formula $2Na_2CO_3 \cdot 3H_2O_2$. Additionally, a perborate, particularly sodium perborate, is used as a solid oxidising agent. The salts are preferably the corresponding alkaline, alkaline-earth or ammonium salts.

The concentration of the oxidising agent in the composition (KM) is determined on the one hand by statutory regulations and on the other hand by the desired effect. According to a preferred embodiment of the According to a preferred embodiment of the present disclosure, the cosmetic product contains the at least one oxidising compound, preferably the percarbonate salt, particularly sodium percarbonate, in a total quantity from about 0.5 to about 25 wt %, preferably from about 2 to about 18 wt %, more preferably from about 4 to about 16 wt %, particularly from about 6 to about 14 wt %, relative to the total weight of the cosmetic product.

The cosmetic composition (KM) contains two or more thickening agents as the second essential ingredient b).

Within the scope of the present disclosure, the term "thickening agent" is understood to refer to compounds which are able to bind liquids, particularly water, and increase the viscosity of said liquids. For the purpose of the present disclosure, these also include gelling agents which are able to thicken liquids to form compositions with gel-like consistency, or gels. "Within the scope of the present disclosure, the terms "thickening agent" and "thickener" are used synonymously. As contemplated herein, gel-like cosmetic media or gels are shape-retaining, readily deformable dispersed systems including at least two components, the gelling agent (usually a solid, colloidally dispersed substance with long or heavily branched compounds) and a liquid (usually water) as the dispersant. The gelling agent forms a spatial network in the liquid, wherein the individual gelling compounds adhere to each other on the basis of primary and/or secondary valences at various spatial points.

Let the two or more thickening agents represent a mixture of at least two different polysaccharides, more preferably a mixture of one at least partially ionic polysaccharide and one substantially non-ionic polysaccharide. Within the scope of the present disclosure, let a substantially non-ionic polysaccharide be a polysaccharide in which the number of monosaccharide units with at least one ionic group is below about 5% of the total number of monosaccharide units.

As noted earlier, it has proven to be particularly challenging to create a cosmetic product for colouring hair which uses solid substances and not liquid hydrogen peroxide as one component for the oxidising agent, and at the same time comprises a thickener which advantageously adjusts the viscosity of the ready-to-use cosmetic product. The problem can be attributed to the fact that thickening agents, which are polyelectrolytes, lose their viscosity increasing properties as the salt content increases. It has proven to be particularly advantageous if a mixture of two different polysaccharides is used as the thickening agent.

According to a preferred embodiment of the present disclosure, the cosmetic product two or more thickening agents are a mixture of a cellulose gum, a hydroxyethylcellulose and a xanthan gum. Surprisingly, it was found that the combination of thickening agents results in a cosmetic composition (KM) that is more easily manageable. When the composition (KM) as contemplated herein composition (KM) containing the three special thickening agents is mixed with the dye composition (FZ) and water, for the first few seconds of mixing the mixture remains fluid, with the result that mixing can be performed easily and quickly. The viscosity then increases and can be spread onto the keratinous fibres easily due to the greater viscosity. After the time usually required for mixing and applying, a maximum viscosity is reached. At this point, the mixture already applied does not drip off the hair. The advantages of improved manageability of the product as contemplated herein for changing the natural colour of keratinous fibres are thus achieved as a result of the slow increase in viscosity obtained through the use of the thickening agents.

According to a preferred embodiment of the present disclosure, the at least one thickening agent is contained in the cosmetic product in a total quantity from about 1 to about 25 wt %, more preferably from about 2 about to 15 wt %, more preferably from about 3 to about 8 wt %, particularly from about 4 to about 6 wt % relative to the total weight of the cosmetic product.

Intensive investigations have surprisingly revealed that a mixture of three thickening agents is particularly favourable for achieving the advantageous effect in terms of viscosity. A particularly preferred embodiment of the present disclosure is therefore a cosmetic product in which the at least one thickening agent is a mixture including a cellulose gum, a hydroxyethylcellulose and a xanthan gum, wherein the quantity of cellulose gum constitutes from about 0.2 to about 10 wt %, more preferably from about 0.5 to about 3 wt %, the quantity of xanthan gum constitutes from about 0.1 to about 5 wt %, more preferably from about 0.5 to about 2 wt %, and/or the quantity of hydroxyethylcellulose constitutes from about 0.2 to about 10 wt %, more preferably from about 0.5 to about 3 wt %, relative to the total weight of the cosmetic product in each case.

Within the scope of the present disclosure, the use of xanthan gums with an average particle diameter $D_{50}$ from about 140 to about 200 µm and a viscosity (about 0.3 wt % solution in about 0.3% KCl) from about 250 to about 800 mPas (measured with Brookfield viscometer at about 3 rpm) have proven to be particularly advantageous. Xanthan gums of such kind are available commercially unter the trade name Keltrol CG-SFT from company CP Kelco, for example.

For the purposes of the present disclosure, the term "xanthan gums" is understood to mean naturally occurring polysaccharides which may be obtained from sugar containing substrates using bacteria of the *Xanthomonas* species. The xanthan gum used as contemplated herein preferably contains d-glucose, d-mannose, d-glucuronic acid, acetate and pyruvate in a molar ratio of about 28:30:20:17:5.1-6.3, wherein the primary chain includes β-1,4-bound glucose units (also called a cellulose chain). The xanthan gums which are used particularly preferably within the scope of the present disclosure have CAS Registry Number 11138-66-2 and the following structural formula

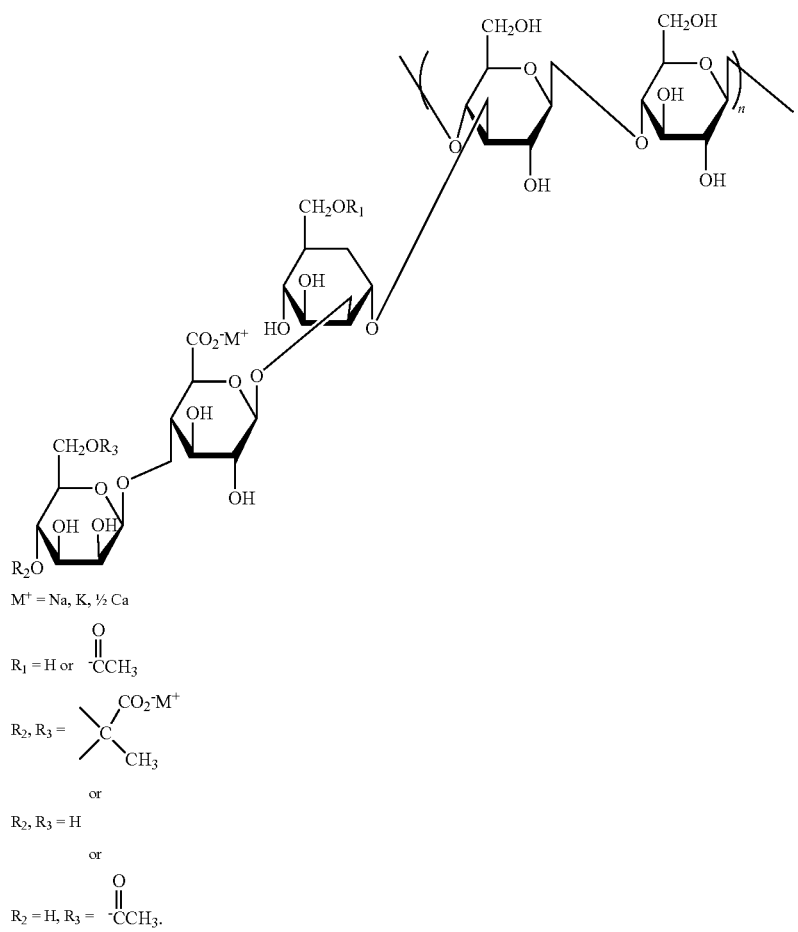

M⁺ = Na, K, ½ Ca

R₁ = H or $-\overset{O}{\underset{\|}{C}}CH_3$

R₂, R₃ = $\overset{CO_2^-M^+}{\underset{CH_3}{C}}$ or

R₂, R₃ = H or

R₂ = H, R₃ = $-\overset{O}{\underset{\|}{C}}CH_3$.

By virtue of its structure, xanthan gum represents a polyelectrolyte. The other specific thickening agents, cellulose gum (carboxymethylcellulose) and hydroxyethylcellulose are available commercially with product names Cekol 5000 and Tylose H 100.000 YP2 respectively. Hydroxyethylcellulose is a cellulose ether and contains substantially no free acid groups.

In the course of the work leading to this present disclosure, it was found that the cosmetic composition (KM) that contain the solid oxidising agents can be thickened well by using the aforementioned specific thickening agents, particularly the preferred mixtures. These cosmetic products are particularly easily manageable.

According to a preferred embodiment of the present disclosure, the cosmetic product contains no hydrogen peroxide. By this it is meant that the cosmetic product is substantially free of hydrogen peroxide, in particular that no hydrogen peroxide is added to the cosmetic product during its composition. Of course, traces of water may be found in the cosmetic product, and these may form hydrogen peroxide wuring the reaction with the solid oxidising agent. But this should only lead to the formation of a small quantity of free hydrogen peroxide. Naturally, hydrogen peroxide may also exist formally in the molecular formula of the solid oxidising agent, in the crystalline structure of the solid oxidising agents and/or as an addition compound with a salt. In these cases also, it is not present as free hydrogen peroxide.

The intended use of the product as contemplated herein is to change colouring oxidatively. The dye composition (FZ) may contain various ingredients depending on the colour that is to be produced. If oxidative dyeing is desired, the dye composition contains the oxidising dye precursors as well as the alkalising agent.

The product as contemplated herein is used for the purpose of changing colour oxidatively. For this purpose, the preparation (KM) which represents the oxidising agent preparation is mixed with the constituent (ii), i.e. with at least the one cosmetic dye composition (FZ) to produce the ready-to-use dyeng agent. In order to prevent incompatibilities and/or to prevent a premature reaction, the preparations (KM) and (FZ) may be packaged separately from one another (double chamber sachet).

As contemplated herein, the cosmetic product may preferably comprises a dye composition (FZ) which is packaged separately from the preparation (KM), wherein the dye composition (FZ) contains at least one compound selected from the oxidising dye precursors, direct colouring agents, alkalising agents, and mixtures thereof.

According to a preferred embodiment of the present disclosure, the cosmetic dye composition (FZ) contains p-toluenediamine sulfate, hydroxyethyl-p-phenylenediamine, m-aminophenol and resorcinol, wherein more preferably the quantity of p-toluenediamine sulfate constitutes from about 0.1 to about 20 wt %, more preferably from about 0.5 to about 5 wt %, the quantity of hydroxyethyl-p- phenylenediamine constitutes from about 0.1 to about 20 wt %, more preferably from about 0.5 to about 5 wt %, the quantity of m-aminophenol constitutes from about 0.1 to about 10 wt %, preferably from about 0.5 to about 3 wt %, or the quantity of resorcinol constitutes from about 0.1 to about 10 wt %, preferably from about 0.5 to about 3 wt % relative to the total weight of the cosmetic product in each case.

According to a preferred embodiment of the present disclosure, the cosmetic product comprises a packaging product wherein the cosmetic composition (KM) is contained in a first compartment of the packaging, and the cosmetic dye composition (FZ) is contained in a second compartment of the packaging, or the cosmetic composition (KM) and the cosmetic dye composition (FZ) are contained together in one compartment of the packaging, wherein the packaging includes a water-soluble film.

The advantage of this preferred embodiment resides in the easy manageability of the cosmetic product. The packaged cosmetic product is dissolved in water, particularly tap water. The solid oxidising agent and the water together develop an active oxygen species which initiates the oxidative treatment.

According to a particularly preferred embodiment of the present disclosure, the water-soluble film is a film on a polyvinyl alcohol base, wherein the polyvinyl alcohol has a deacetylation degree of about 85% and more, more preferably of about 87% and more, most preferably of about 89%, and/or polyvinyl alcohol has a weight-average molecular weight $M_w$ from about 70,000 g/mol to about 120,000 g/mol, more preferably from about 80,000 g/mol to about 110,000 g/mol, most preferably from about 90,000 to about 100,000 g/mol, measured by GPC chromatography in water with a polydispersity index from about 3.1 to about 4.5, more preferably from about 3.5 to about 4.1. The molecular weights are examined by gel permeation chromatography (GPC) and compared with each other. During sample preparation for determining the molecular weights, the sample patterns were dissolved in distilled water overnight and after routine filtration separated on a Suprema column set designed for aqueous solvents. A solvent mixture on a base of sodium chloride and sodium hydrogen phosphate was used as the eluent, and chromatography was carried out with a UV and IR detector and a column oven temperature of about 30° C.

It is known that polyvinyl alcohol is produced by polymerisation of vinyl acetate and subsequent hydrolysis of the acetate groups. It was found that a preferred degree of hydrolysis is advantageous for use as the packaging film. The degree of hydrolysis can be determined by NMR spectroscopy and indicates the number of hydrolysed monomers as a percentage of the total number of monomers.

It was also found, surprisingly, that a preferred molecular weight is advantageous for the use of the cosmetic product. The films LXP9646, LXP20633, XP20013 manufactured by Monosol or the film Solublon GS BTX #40 manufactured by Aicello are used as products.

Cosmetic products in the related art are most often packaged in films which are different from the preferably used films: Conventional cosmetic dyeing or blonding products are contained in packaging products that comprise at least one multi-ply film (F). This film contains at least a first polymer layer (P1), at least a second polymer layer (P2) and at least a barrier layer (BS). This multi-ply film constitutes the wall or the outer envelope of the packaging. Such a packaging product is usually created by bonding, crimping or welding two superimposed pieces of film (wherein the packaging (VP) is simultaneously filled with the cosmetic composition (KM)), i.e. a packaging product of such kind is sealed at all edges. This packaging product may be opened for example by ripping or cutting it open.

The term "packaging" is further understood to refer to a packaging product in the form of a sachet. In a special embodiment which is described below, the packaging may also be a double sachet. A sachet (pouch) is a small packaging product in the form of a pocket or a pouch which is often used for packaging cosmetics. The capacity of the packaging, particularly the sachet, may be for example from about 5 to about 1000 ml, preferably from about 10 to about 200 ml and particularly preferably from about 20 to about 50 ml.

A double sachet is a sachet which includes two separate chambers. Even the division by measured quantities is more economical in terms of space in a double sachet than the portioning of hydrogen peroxide in a plastic bottle. Handling of the cosmetic product is simplified significantly by the use of a double sachet. In the one chamber, the cosmetic composition comprising the oxidising agent is contained, the other chamber contains the dye composition including the developer components and coupler components. The creation of the cosmetic product in the form of a double sachet offers the advantage of space saving storage and easier handling.

The sachet or the double sachet which holds components (i) and (ii) may easily be mixed with water, in which case the packaging then dissolves. Then, the solid oxidising agent and the cosmetic dye composition come into contact with each other and can react to form a ready-to-use cosmetic composition.

According to one embodiment, a cosmetic product is provided in which the packaging product is a single-chamber sachet in which the cosmetic composition (KM) and the cosmetic dye composition are present. This embodiment represents a product which is particularly easy to handle. Surprisingly, it was found that the combination of the water-soluble film, the solid oxidising agent and the thickening agent, in particular the preferred mixture of several thickening agents completely solves the problem the present disclosure is intended to address.

Alternatively, the packaging product may be a two-chamber pouch in which the cosmetic composition (KM) is contained in a first chamber of the two-chamber pouch, and the cosmetic dye composition (FZ) is contained in a second chamber of the two-chamber pouch.

According to one embodiment, a cosmetic product is provided in which the two-chamber pouch comprises a first multi-ply film (F1), forming the packaging of the first chamber, and a second multi-ply film (F2) forming the packaging of the second chamber, wherein the material of the film is completely soluble in water.

According to one embodiment, the first chamber and the second chamber of the double chamber sachet are separated from one another at least by a sealed seam, and the two-chamber pouch is furnished with a perforation which when parted opens both chambers of the two-chamber pouch. When the perforation is separated, an opening is created in each chamber, through which the contents of the first chamber and the contents of the second chamber can exit. The feature according to which the to chambers of the two-chamber pouch should have a form in which they are separated "at least" by one sealed seam, is intended to mean that further features may also be realised between the pouches, for example a perforation may be provided along the sealed seam, which when parted serves to separate the two chambers of the two-chamber pouch. Alternatively, the separation of the two chambers may be assured by a film. In this case, when viewed from the outside the double sachet looks like a single sachet, wherein the chambers are separated from each other only by the film, or optionally by a double film, wherein the separating film or separating double film is disposed between the two outer films.

The conventional packaging of cosmetic product may be exemplified by the following construction and the following properties: The arrangement of the layers (P1), (P2) and (BS) within the multi-ply film (F) may vary. Moreover, it is also possible that the film (F) comprises still more layers besides those listed. It is also advantageous if all of the layers mentioned previously are each orientated parallel to the surfaces of the film (F), that is to say all layers have the same orientation.

It may be provided that the barrier layer (BS) is arranged on the side that comes into contact with the cosmetic composition (KM). The first polymer layer (P1) is thus bordered on one side by the barrier layer (BS) and on the other by the second polymer layer (P2), which is on the outside of the packaging. In this context, the polymer layer (P1) is different from the polymer layer (P2). In this context, the barrier layer (BS) functions as a carrier layer, on which the first polymer layer (P1) is then deposited. The second polymer layer (P2) is then deposited on this polymer layer (P1). The three layers (BS), (P1) and (P2) together form a film (F) whose total thickness is preferably in the range from 30 μm to 1.0 mm.

The barrier layer (BS) lies between the first polymer layer (P1) and the second polymer layer (P2). In this case, the multi-ply film (F) includes three layers, wherein the layer (P1) is located innermost and is in contact with the cosmetic composition (KM). The layer (P1) is in contact with the barrier layer (BS), and the barrier layer (BS) in turn is in contact with the layer (P2). With this layer, the layers (P1) and (P2) are not adjacent to one another, but are separated by the barrier layer (BS). In this arrangement, in principle the layers (P1) and (P2) may be made from the same polymer material, though it is preferable that the two layers (P1) and (P2) be made from different polymer materials. Together, the three layers (P1), (BS) and (P2) form a film (F) whose total thickness is in the range from about 30 μm to about 1.0 mm. The particular advantage of this arrangement resides in the fact that the—often very thin—barrier layer (BS) is positioned neither on the inner nor the outer surface of the multi-ply film (F), but is protected inwardly by the polymer layer (P1) and outwardly by the polymer layer (P2). Thus, it is possible to prevent a mechanical abrasion or a mechanical destruction of the barrier layer (BS) in the most effective way possible in this arrangement. It is therefore advantageous if the at least one multi-ply film (F) includes the at least one barrier layer (BS) between the at least one first polymer layer (P1) and the at least one second polymer layer (P2).

A film (F) is also disclosed in which the first polymer layer (P1) is arranged on the side which is in contact with the cosmetic composition (KM). The second polymer layer (P2) is adjacent to the polymer layer (P1) and is different from it. The barrier layer (BS) is located on the outside. In films (F) with this layer arrangement, the layer (P1) may function as a polymer carrier layer, for example, on which the second polymer layer (P2) is then placed. Subsequently the side adjacent to (P2) (i.e. the outside) is provided with the barrier layer. It is therefore advantageous if the at least one multi-ply film (F) includes the at least one barrier layer (BS) on the outer side of the packaging (VP). The outer side of the packaging (VP) is understood to be the side of the packaging which does not come into contact with the cosmetic composition (KM), but is exposed to the environment. The three layers (P1), (P2) and (BS) thus form a film (F) whose total thickness is preferably in the range from about 30 μm to about 1.0 mm. The use of such packaging products has proven particularly advantageous for purposes of enhanced storage stability, since this arrangement shows neither swelling nor delamination upon prolonged exposure to a composition that contains oxidising agents.

In addition, the preparation (KM) may also further contain one or more acids for stabilising the oxidising agent used. It is therefore preferable within the scope of the present disclosure if the cosmetic composition (KM) further contains at least one acid selected from the group of dipicolinic acid, citric acid, acetic acid, malic acid, lactic acid, tartaric acid, hydrochloric acid, phosphoric acid, pyrophosphoric acid and salts thereof, benzoic acid and salts thereof, 1-Hydroxyethane-1,1-diphosphonic acid, ethylenediaminetetraacetic acid and salts thereof, sulfuric acid and mixtures, particularly a mixture of dipicolinic acid, disodium pyrophosphate, ethylenediaminetetraacetic acid and salts thereof, and 1-Hydroxyethane-1,1-diphosphonic acid.

In the following text, further preferred components of the dye composition are listed: Since it is intended that the cosmetic product as contemplated herein should bring about oxidative colouring, the cosmetic dye composition (FZ)—in the following text also referred to as preparation (FZ)—contains at least one oxidising dye precursor. Oxidising dye precursors may be divided into developers and couplers, wherein the developers are mostly used in the form of their physiologically tolerable salts (e.g., in the form of their hydrochlorides, hydrobromides, hydrogen sulfates or sulfates) due to their greater sensitivity to oxygen. During the oxidative colouring process, coupler components alone do not contribute significantly to the colouring, they need the constant presence of developer components. Such media preferably contain at least one oxidising dye precursor of the developer type and at least one oxidising dye precursor of the coupler type. In contrast to the preferred selected components, particularly suitable oxidising dye precursors of the developer type are selected from at least one compound in the group including p-Phenylenediamine, p-Toluenediamine, 2-(1,2-Dihydroxyethyl)-p-phenylenediamine, N,N-Bis-(2-hydroxyethyl)-p-phenylenediamine, 2-Methoxymethyl-p-phenylenediamine, N-(4-Amino-3-methylphenyl)-N-[3-(1H-imidazol-1-yl)propyl]amine, N,N'-Bis-(2-hydroxyethyl)-N,N'-bis-(4-aminophenyl)-1,3-diaminopropan-2-ol, Bis-(2-hydroxy-5-aminophenyl)methane, 1,3-Bis-(2,5-diaminophenoxy)propan-2-ol, N,N'-Bis-(4-aminophenyl)-1,4-diazacycloheptane, 1,10-Bis-(2,5-diaminophenyl)-1,4,7,10-tetraoxadecane, p-Aminophenol, 4-Amino-3-methylphenol, 4-Amino-2-aminomethylphenol, 4-Amino-2-(1,2-dihydroxyethyl)phenol, 4-Amino-2-(diethylaminomethyl)phenol, 4,5-Diamino-1-(2-hydroxyethyl) pyrazole, 2,4,5,6-Tetraaminopyrimidine, 4-Hydroxy-2,5,6-triaminopyrimidine, 2-Hydroxy-4,5,6-triaminopyrimidine, 2,3-Diamino-6,7-dihydro-1H,5H-pyrazolo[1,2-a]pyrazol-1-one and the physiologically tolerable salts thereof.

Particularly suitable oxidising dye precursors of the coupler type are selected from the group including 5-Amino-2-methylphenol, 3-Amino-2-chloro-6-methylphenol, 2-Hydroxy-4-aminophenoxyethanol, 5-Amino-4-chloro-2-methylphenol, 5-(2-Hydroxyethyl)-amino-2-methylphenol, 2,4-Dichloro-3-aminophenol, 2-Aminophenol, 3-Phenylenediamine, 2-(2,4-Diaminophenoxy)ethanol, 1,3-Bis(2,4-diaminophenoxy)propane, 1-Methoxy-2-amino-4-(2-hydroxyethylamino)benzene, 1,3-Bis(2,4-diaminophenyl) propane, 2,6-Bis(2'-hydroxyethylamino)-1-methylbenzene, 2-({3-[(2-Hydroxyethyl)amino]-4-methoxy-5-methylphenyl}amino)ethanol, 2({3-[(2-Hydroxyethyl)amino]-2-methoxy-5-methylphenyl}amino)ethanol, 2-({3-[(2-Hydroxyethyl)amino]-4,5-dimethylphenyl}amino) ethanol, 2-[3-Morpholine-4-ylphenyl)amino]ethanol, 3-Amino-4-(2-methoxyethoxy)-5-methylphenylamine, 1-Amino-3-bis-(2-hydroxyethyl)aminobenzene, resorcinol, 2-Methylresorcinol, 4-Chlororesorcinol, 1,2,4-Trihydroxybenzene, 2-Amino-3-hydroxypyridine, 3-Amino-2-methyl-amino-6-methoxypyridine, 2,6-Dihydroxy-3,4-dimethylpyridine, 3,5-Diamino-2,6-dimethoxypyridine, 1-Phenyl-3-methylpyrazol-5-one, 1-Naphthol, 1,5-Dihydroxynaphthaline, 2,7-Dihydroxynaphthaline, 1,7-Dihydroxynaphthaline, 1,8-Dihydroxynaphthaline, 4-Hydroxyindole, 6-Hydroxyindole, 7-Hydroxyindole, 4-Hydroxyindoline, 6-Hydroxyindoline, 7-Hydroxyindoline or mixtures of these compounds or the physiologically tolerable salts thereof.

As contemplated herein, the dye composition (FZ) may contain or more direct colouring agents. Suitable non-ionic direct colouring agents may be selected from the group including HC Yellow 2, HC Yellow 4, HC Yellow 5, HC Yellow 6, HC Yellow 12, HC Orange 1, Disperse Orange 3, HC Red 1, HC Red 3, HC Red 7, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9,1,4-Diamino-2-nitrobenzene, 2-Amino-4-nitrophenol, 1,4-Bis-(2-hydroxyethyl)-amino-2-nitrobenzene, 3-Nitro-4-(2-hydroxyethyl) aminophenol, 2-(2-Hydroxyethyl)amino-4,6-dinitrophenol, 4-[(2-Hydroxyethyl)amino]-3-nitro-1-methylbenzene, 1-Amino-4-(2-hydroxyethyl)amino-5-chloro-2-nitrobenzene, 4-Amino-3-nitrophenol, 1-(2'-Ureidoethyl)amino-4-nitrobenzene, 2-[(4-Amino-2-nitrophenyl)amino]benzoic acid, 4-[(3-Hydroxypropyl)amino]-3-nitrophenol, 4-Nitro-o-phenylenediamine, 6-Nitro-1,2,3,4-tetrahydroquinoxaline, 2-Hydroxy-1,4-naphthoquinone, picramic acid and salts thereof, 2-Amino-6-chloro-4-nitrophenol, 4-Ethylamino-3-nitrobenzoic acid and 2-Chloro-6-ethylamino-4-nitrophenol.

Suitable anionic direct colouring agents may be selected from the group including Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, Bromophenol Blue and Tetrabromophenol Blue.

Suitable cationic direct colouring agents are cationic triphenylmethane colouring agents, such as for example Basic Blue 7, Basic Blue 26, Basic Violet 2 and Basic Violet 14, aromatic systems that are substituted with a quaternary nitrogen group, such as for example Basic Yellow 57, Basic Red 76, Basic Blue 99, Basic Brown 16 and Basic Brown 17, cationic anthraquinone colouring agents such as HC Blue 16 (Bluequat B) and direct colouring agents which contain a heterocyclic compound which has at least one quaternary nitrogen atom, particularly Basic Yellow 87, Basic Orange 31 and Basic Red 51. The cationic direct colouring agents which are marketed under the trademark Arianor are also cationic direct colouring agents which are suitable as contemplated herein.

Dyeing processes on keratinous fibres typically take place in an alkaline environment. In order to minimise stress on the skin as well as on the keratinous fibres as far as possible, however, it is not desirable to set an excessively high pH value. Therefore, it is preferable if the pH value of the preparation (FZ) lies between about 7 and about 11, particularly between about 8 and about 10.5. pH values within the meaning of the present disclosure, are pH values that have been measured at a temperature of about 22° C.

The cosmetic product or preparation (FZ) may contain at least one alkalising agent. The alkalising agents which are usable as contemplated herein to set the preferred pH value may be selected from the group including ammoniac, alkanolamines, basic amino acids, and inorganic alkalising agents such as (earth)alkali metal hydroxides, (earth)alkali metal metasilicates, (earth)alkali metal phosphates and (earth)alkali metal hydrogen phosphates. Preferred inorganic alkalising agents are magnesium carbonate, sodium hydroxide, potassium hydroxide, sodium silicate and sodium metasilicate.

The cosmetic product particularly preferably also contains at least one inorganic alkalising agent which is solid at about 20° C. and about $10^5$ Pa, of which at least one sodium silicate or sodium metasilicate with a molar $SiO_2/Na_2O$ ratio of ≥2, preferably from about 2.5 to about 3.5, in a total quantity from about 10 to about 50 wt %, preferably from about 20 to about 40 wt % relative to the total weight of the cosmetic product in each case.

Organic alkalising agents that are usable as contemplated herein are preferably selected from monoethanolamine, 2-Amino-2-methylpropanol and Triethanolamine. The basic amino acid that are usable as contemplated herein as alkalising agents are preferably selected from the group including arginine, lysine, ornithine and histidine, particularly preferably arginine. However, it was found in the course of the research conducted for the present disclosure that media which are preferred as contemplated herein also contain an organic alkalising agent. One embodiment of the first object of the present disclosure agent further contains at least one alkalising agent which is selected from the group including ammoniac, alkanolamines and basic amino acids, particularly ammoniac, monoethanolamine and arginine or compatible salts thereof.

The cosmetic product or preparation (FZ) may further contain additional active substances, adjuvants and additives. Thus for example one or more fatty constituents from the group of $C_{12}$-$C_{30}$-fatty alcohols, $C_{12}$-$C_{30}$ fatty acid triglycerides, $C_{12}$-$C_{30}$ fatty acid monoglycerides, $C_{12}$-$C_{30}$ fatty acid diglycerides and/or hydrocarbons may be contained.

A surface-active substance may preferably also be added to the preparation (FZ) or the cosmetic product, such surface-active substances being described as tensides or as emulsifiers: They are preferably selected from anionic, zwitterionic, amphoteric and non-ionic tensides and emulsifiers.

The preparation (FZ) or cosmetic product preferably contains at least one anionic tenside. Preferred anionic tensides are fatty acids, alkyl sulfates, alkylether sulfates and ether carboxylic acids with 10 to 20 C atoms in the alkyl group and up to 16 glycol ether groups in the molecule.

The preparation (FZ) or cosmetic product may further contain at least one zwitterionic tenside. Preferred zwitterionic tensides are betaine, N-Alkyl-N,N-dimethylammonium-glycinate, N-Acyl-aminopropyl-N,N-dimethylammoniumglycinate, and 2-Alkyl-3-carboxymethyl-3-hydroxyethyl-imidazoline. One preferred zwitterionic tenside is known under the INCI designation Cocamidopropyl Betaine.

Additionally, it may be provided that the preparation (FZ) or the cosmetic product contains at least one amphoteric tenside. Preferred amphoteric tensides are N-Alkylglycine, N-Alkylpropionic acids, N-Alkylaminobutyric acids, N-Alkyliminodipropionic acids, N-Hydroxyethyl-N-alkylamidopropylglycine, N-Alkyltaurine, N-Alkylsarcosine, 2-Alkylaminopropionic acids and Alkylaminoacetic acids. Particularly preferred amphoteric tensides are N-Coconut alkylaminopropionate, Coconut aacylaminoethylaminopropionate, and $C_{12}$-$C_{18}$ acyl sarcosine.

It has further proven advantageous if the preparation (FZ) or the cosmetic product contain further, non-ionogenic boundary surface active substances. Preferred non-ionic tensides are alkylpolyglycosides and alkyleneoxide adducts from fatty alcohols and fatty acids, each having from about 2 to about 30 mol ethylene oxide per mol fatty alcohol or fatty acid. Preparations with excellent properties are also obtained when they contain fatty acid esters of ethoxylated glycerol as non-ionic tensides.

The non-ionic, zwitterionic or amphoteric tensides are used in quantities constituting from about 0.1 to about 45 wt %, preferably from about 1 to about 30 wt % and most particularly preferably from about 1 to about 15 wt % of the total weight of the cosmetic product.

The preparation (FZ) or cosmetic product may further contain additional active substances, adjuvants and additives such as for example non-ionic polymers such as vinylpyrrolidone/vinylacrylate copolymer, polyvinylpyrrolidone, vinylpyrrolidone/vinylacetate copolymer, polyethylene glycols and polysiloxanes; additional silicones such as volatile or non-volatile straight chain, branched or cyclic, cross-linked or non-cross-linked polyalkylsiloxanes (such as dimethicone or cyclomethicone), polyarylsiloxane and/or polyalkylarylsiloxanes, particularly polysiloxaned with organofunctional groups, such as substituted or unsubstituted amines (amodimethicone), carboxyl-, alkoxy- and/or hydroxyl groups (dimethicone copolyols), linear polysiloxane(A)-polyoxyalkylene(B) block copolymers, grafted silicone polymers; cationic polymers such as quaternised cellulose ethers, polysiloxanes with quaternised groups, dimethyldiallylammonium chloride polymers, acrylamide-dimethyldiallyl-ammonium chloride copolymers, dimethyl-amino-ethylmethacrylate-vinylpyrrolidone copolymer quaternised with diethyl sulfate, vinylpyrrolidone-imidazolinium-methochloride copolymer and quaternised polyvinyl alcohol; zwitterionic and amphoteric polymers; anionic polymers such as for example polyacrylic acids or cross-linked polyacrylic acids; structuring substances such as glucose, maleic acid and lactic acid, hair conditioning compounds such as phospholipids, for example lecithin and cephalin; perfume oils, dimethyl isosorbide and cyclodextrin; agents for improving fibre structure, particularly mono-, di- and oligosaccharides such as glucose, galactose, fructose, fruit sugar and lactose; colouring agents for colouring the agent; anti-dandruff ingredients such as Piroctone Olamine, Zink Omadine and Climbazol; Aminoacids and Oligopeptide; protein hydrolysates of animal and/or vegetable origin, and in the form of their fatty acid condensation products or optionally anionically or cationically modified derivatives; fats and vegetable oils; light stabilisers and UV blockers; active substances such as panthenol, pantothenic acid, pantolactone, allantoin, pyrrolidone carboxylic acids and their salts as well as bisabolol; polyphenols, particularly hydroxycinnamic acids, 6,7-Dihydroxycoumarin, Hydroxybenzoic acids, catechins, tannins, leukoanthocyanidins, anthocyanidins, flavanones, flavones and flavonols; ceramides or pseudoceramides; vitamins, provitamins and vitamin precursors; plant extracts; fats and waxes such as fatty alcohols, beeswax, montan wax and paraffins; swellng and penetrating agents such as glycerol, propylene glycol monoethylether, carbonates, hydrogen carbonates, guanidines, ureas and primary, secondary and tertiary phosphats; opacifiers such as latex, Styrene/PVP and Styrene/Acrylamide copolymers; pearlescent agents such as ethylene glycol mono- and -distearate as well as PEG-3-distearate and pigments.

The selection of these further substances will be made by the person skilled in the art depending on the desired properties of the preparation (FZ) or cosmetic product and according to the product as contemplated herein. Regarding further optional components and the quantities of such components that are used, reference is herewith made explicitly to the pertinent literature, which will be known to the person skilled in the art. The additional active ingredients and additives are used in the preparation (FZ) or cosmetic product preferably in quantities from about 0.0001 to about 25 wt %, particularly from about 0.0005 to about 15 wt % relative to the total weight of the cosmetic product in each case.

The problem addressed by the present disclosure is further solved by the object of claim 10. A second object of the present disclosure is therefore a method for dyeing keratinous fibres, particularly human hair, which a cosmetic product according to the first object of the present disclosure is mixed with water, applied to the keratin-containing fibres immediately afterwards, left on the fibres for from about 5 to about 60 minutes, and the fibres are then rinsed with water and optionally washed out with a tenside-containing cleaning agent. According to a preferred embodiment of the method as contemplated herein, the cosmetic product and water are mixed with each other in a weight-relative mixture ratio between the cosmetic product and the water from about 1 to 1 to about 1 to 5, preferably from about 1 to 1 to about 1 to 4, most preferably from about 1 to 1 to about 1 to 3.

Of course, particular features of the first object which are only described in that context apply correspondingly as preferred features in respect of the second object of the present disclosure.

The following examples are intended to explain the present disclosure without thereby limiting the present disclosure:

EXAMPLES

A PVOH film having a weight average molar weight of 93,590 g/mol with polydispersitindex of 3.8 is used for the packaging products.

The film Monosol SXP 20633 is also used.

The packaging products (VP) were each filled with the following preparations (KM) (all values in wt %).

| Contents | KM1 | KM2 | KM3 | KM4 | KM5 | KM6 | KM7 | KM8 |
|---|---|---|---|---|---|---|---|---|
| Carboxymethylcellulose (Cekol 50000) | 1.00 | 1.00 | 1.00 | 1.00 | 1.00 | 1.00 | 1.00 | 1.00 |
| Xanthan Gum (Keltrol CG-SFT) | 0.50 | 0.50 | 0.50 | 0.50 | 0.50 | 0.50 | 0.50 | 0.50 |
| Hydroxyethylcellulose (Tylose H 100000 YP 2) | 1.00 | 1.00 | 1.00 | 1.00 | 1.00 | 1.00 | 1.00 | 1.00 |

-continued

| Contents | KM1 | KM2 | KM3 | KM4 | KM5 | KM6 | KM7 | KM8 |
|---|---|---|---|---|---|---|---|---|
| Sodium sulfate | 0.25 | 0.25 | 0.25 | 0.25 | 0.25 | 0.25 | 0.25 | 0.25 |
| Zinc oxide | 0.40 | 0.40 | 0.40 | 0.40 | 0.40 | 0.40 | 0.40 | 0.40 |
| Sodium metasilicate (anhydrous) | | | | | | | | 0.61 |
| Paraffinum Liquidum | | | | | 0.38 | | 0.35 | 0.22 |
| p-Toluenediaminesulfate | | | 0.33 | 0.39 | 0.15 | 0.53 | 0.37 | 2.58 |
| Hydroxyethyl-p-phenylendiamine | 1.0 | | | | | | | |
| HydroxyET 4,5-Diamino Pyrazolsulfate, 1- | | 1.0 | | | | | 0.45 | |
| m-Aminophenol | 0.04 | 0.36 | 0.03 | 0.01 | | 0.04 | 0.06 | 0.35 |
| 2,7-Dihydroxynaphthalene | 0.04 | | | | | | | |
| 2-Methylresorcinol | 0.09 | | 0.39 | 0.07 | | 0.02 | | |
| Resorcinol | 0.02 | | 0.04 | 0.09 | 0.27 | 0.17 | 0.04 | 0.84 |
| p-Amino-o-cresole | | 0.15 | | | 0.26 | | 0.32 | |
| 2-Amino-3-hydroxypyridine | | | 0.08 | 0.04 | 0.26 | 0.04 | | |
| 2-Amino-3-methylphenol, 4- | | | | | 0.47 | | 0.06 | |
| 2-Amino-6-chloro-4-nitrophenol | | | | | 0.24 | | | |
| 4-Chlororesorcinol | 0.06 | | | | | | | |
| 2-Amino-4-HydroxyETaminoanisole Sulfate | | | | | | | 0.04 | |
| 2,4-Diaminophenoxy-ethanol 2HCl | | | | | | | | 1.65 |
| Sodium percarbonate | 12.00 | 24.00 | 23.00 | 12.00 | 20.00 | 19.00 | 16.00 | 12.00 |
| Fragrance | | | | | | | | 0.10 |
| Sodium carbonate | 1.40 | 1.40 | 1.40 | 1.40 | 1.40 | 1.40 | 1.40 | |

Cosmetic compositions KM1 to KM8 were introduced into double sachets. Then the packaging products were stored at 40° C. for 24 weeks. Ready-to-use dye compositions may be produced by stirring with water.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A cosmetic product for changing the natural colour of keratinous fibres, comprising
   (i) at least one cosmetic composition (KM) comprising:
      a) at least one oxidising compound comprising percarbonate salt present in an amount of from about 6 to about 25 wt %, and
      b) two or more thickening agents consisting of a mixture of a cellulose gum, a hydroxyethylcellulose and a xanthan gum, and
   (ii) at least one cosmetic dye composition (FZ),
   wherein the cosmetic product further comprises a packaging product, wherein
      the cosmetic composition (KM) is included in a first compartment of the packaging product and the cosmetic dye composition (FZ) is included in a second compartment of the packaging product, or
      the cosmetic composition (KM) and the cosmetic dye composition (FZ) are included together in one compartment of the packaging product,
   wherein the packaging includes a water-soluble film, wherein the water-soluble film is a film based on polyvinyl alcohol (PVOH), wherein the polyvinyl alcohol has a deacetylation degree of 85% and more and/or wherein the polyvinyl alcohol has a weight-average molecular weight $M_w$ from about 70,000 g/mol to about 120,000 g/mol, measured by GPC chromatography in water with a polydispersity index from 3.1 to 4.5.

2. The cosmetic product according to claim 1, wherein the two or more thickening agents are included in the cosmetic product in a total quantity from 1 to 25 wt %, relative to the total weight of the cosmetic product.

3. The cosmetic product according to claim 1, wherein the quantity of cellulose gum constitutes from 0.2 to 10 wt % and the quantity of hydroxyethylcellulose constitutes from 0.2 to 10 wt %, relative to the total weight of the cosmetic product in each case.

4. The cosmetic product according to claim 1, wherein the cosmetic dye composition (FZ) comprises p-Toluenediaminesulfate, Hydroxyethyl-p-phenylenediamine, m-Aminophenol and Resorcinol.

5. The cosmetic product according to claim 1, wherein the cosmetic comprises no free hydrogen peroxide.

6. The cosmetic product according to claim 1, further comprising at least one inorganic alkalising agent which is solid at 20° C. and $10^5$ Pa including at least one sodium silicate or sodium metasilicate with a molar $SiO_2/Na_2O$ ratio of $\geq 2$.

7. A method for colouring keratinous fibres, the method comprising:
   mixing a cosmetic product according to claim 1 with water to form a mixture,
   applying the mixture to the keratinous fibres immediately thereafter, leaving the mixture on the keratinous fibres for 5 to 60 minutes, and rinsing the keratinous fibres with water and optionally washing the keratinous fibres with a tenside-containing cleaning agent.

8. The cosmetic product of claim 1, wherein the cellulose gum is present in an amount of from about 0.2 to about 10 wt %, the hydroxyethylcellulose is present in an amount of from about 0.2 to about 10 wt %, and the xanthan gum is present in an amount of from about 0.1 to about 5 wt %, relative to the total weight of the cosmetic product in each case.

9. The cosmetic product of claim 8, wherein the cellulose gum is present in an amount of from about 0.5 to about 3 wt %, the hydroxyethylcellulose is present in an amount of from about 0.5 to about 3 wt %, and the xanthan gum is present in an amount of from about 0.5 to about 2 wt %, relative to the total weight of the cosmetic product in each case.

10. The cosmetic agent of claim 8, wherein the total amount of thickening agents in the cosmetic product is from about 3 to about 8 wt %, based on the total weight of the cosmetic product.

\* \* \* \* \*